(12) United States Patent
Erickson et al.

(10) Patent No.: US 7,652,053 B2
(45) Date of Patent: Jan. 26, 2010

(54) DIAMINOCYCLOALKANE MCH RECEPTOR ANTAGONISTS

(75) Inventors: Shawn David Erickson, Leonia, NJ (US); Yimin Qian, Wayne, NJ (US); Jefferson Wright Tilley, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 255 days.

(21) Appl. No.: 11/942,106

(22) Filed: Nov. 19, 2007

(65) Prior Publication Data

US 2008/0146636 A1 Jun. 19, 2008

Related U.S. Application Data

(60) Provisional application No. 60/861,867, filed on Nov. 30, 2006.

(51) Int. Cl.
*A61K 31/4184* (2006.01)
*C07D 235/04* (2006.01)

(52) U.S. Cl. .................................. 514/394; 548/309.7
(58) Field of Classification Search ........................ None
See application file for complete search history.

(56) References Cited

U.S. PATENT DOCUMENTS 6,291,499 B1 9/2001 Thompson et al.

FOREIGN PATENT DOCUMENTS

WO WO 03/060475 A2 7/2003
WO WO 2004/031177 A1 4/2004
WO WO 2007/039462 A2 4/2007

OTHER PUBLICATIONS

Moriya, Minoru, et al—Chemical Abstract Service, Preparation of 2-aminobenzimidazole derivates as antagonists of melanin-concentrating hormone receptor XP002469711.

*Primary Examiner*—Kamal A Saeed
(74) *Attorney, Agent, or Firm*—George W. Johnston; Dennis P. Tramaloni; Samuel H. Megerditchian

(57) ABSTRACT

Provided herein are compounds of the formula (I):

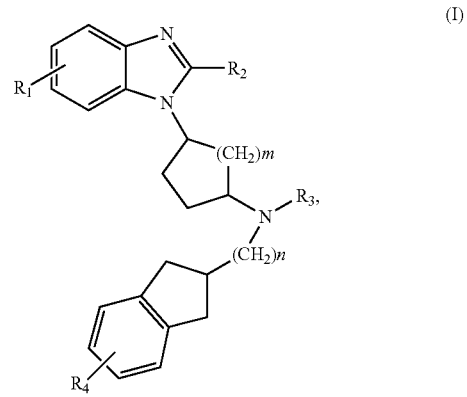

as well as pharmaceutically acceptable salts thereof, wherein the substituents are as those disclosed in the specification. These compounds, and the pharmaceutical compositions containing them, are useful for the treatment of obesity, hyperphagia, anxiety, depression and related disorders and diseases.

19 Claims, No Drawings

DIAMINOCYCLOALKANE MCH RECEPTOR ANTAGONISTS

PRIORITY TO RELATED APPLICATION(S)

This application claims the benefit of U.S. Provisional Application No. 60/861,867, filed Nov. 30, 2006, which is hereby incorporated by reference in its entirety.

FIELD OF THE INVENTION

The invention relates to melanin-concentrating hormone receptor antagonists and derivatives thereof. The antagonists and derivatives thereof are useful for the treatment of obesity, hyperphagia, anxiety, depression and related disorders and diseases.

All documents cited or relied upon below are expressly incorporated herein by reference.

BACKGROUND OF THE INVENTION

Melanin-concentrating hormone (MCH) is a cyclic peptide that was first isolated from the pituitary of chum salmon (Kawauchi et al. (1983) Nature 305: 321-333). The sequence for MCH has been shown to be identical in all teleost fish where it causes melanin granulation and, hence, regulates color change. Recent reports also suggest MCH plays a role in food intake in teleosts. MCH also inhibits release of ACTH thus acting as an antagonist of α-MSH. MCH was subsequently identified in mammals as a cyclic nonapeptide. The first MCH receptor (later termed MCHR1) is a G-protein coupled receptor (GPCR) and was identified using a "reverse pharmacology" approach. That is, it was demonstrated that the natural ligand of orphan GPCR, SLC-1, was MCH in mammals. Subsequent to this determination, a second MCH receptor (MCHR-2) has been identified. The role of MCH in feeding behavior in mammals has been the subject of investigation for a number of years (Qu, et al. (1996) Nature, 380: 243-247; Rossi et al. (1997) Endocrinology 138: 351-355; Shimada et al. (1998) Nature 396: 670-674). MCH is predominantly expressed in the lateral hypothalamus and the zona incerta of the central nervous system (CNS). Central administration of MCH is known to stimulate food intake and regulate energy balance. MCH is upregulated in the lateral hypothalamus during fasting (Rossi et al. (1997) Endocrinology 138: 351-355). Knockout experiments have shown that mice lacking the MCH peptide are lean, hypophagic and maintained elevated metabolic rates. MCH mRNA levels are increased in both normal and obese mice. Transgenic mice that over-express MCH are obese and insulin resistant. Genetically altered animals that lack the gene encoding the MCH receptor are moderately hyperphagic but show resistance to becoming obese and have an increased metabolic rate (Shimada et al. (1998) Nature 396: 670-674). MCH is thought to exert its effects on feeding behavior by binding to an MCH receptor (MCHR1 or MCHR2) resulting in mobilization of intracellular calcium and a concomitant reduction in cyclic AMP levels. The consistency in these findings suggests that MCH antagonism could safely lead to weight loss in humans. In further support of this, a number of studies describe statistically significant reduction of food intake in rodents following acute administration of MCH receptor antagonists and/or statistically significant reduction of body weight after chronic administration of small molecule MCH receptor antagonists (Borowsky et al. (2002) Nature Medicine 8(8):825-830; Souers et al. (2005) Bioorg. Med. Chem. Lett. 15: 2752-2757; Vasudevan et al. (2005) Bioorg. Med. Chem. Lett. 15: 4174-4179; Kym et al. (2005) J. Med. Chem. 5888-91; McBriar et al. (2005) J. Med. Chem. 48: 2274; Takekawa et al. (2002) Eur. J. Pharmacol. 438(3): 129-135; Kowalski et al. Eur. J. Pharmacol. (2004) 497: 41-47). The precise role of MCH in attenuating food intake is not clear from these studies because the small-molecule MCH receptor antagonists described are either 1) unselective for the MCH receptor or 2) no selectivity data is disclosed.

MCHR1 antagonism with a small molecule is now recognized as a promising strategy for the treatment of obesity. The following relate to small-molecule MCH receptor antagonists: Kato et al. WO2001/21577; Chen et al. WO2002/089729; Collins et al. WO2003/105850; Souers et al. US2005/0137243; Hulme et al. WO2005/019167; Tempest et al. WO2005/019240; Barvian et al. WO2004092181; Barvian et al. WO2005/042541; McKittrick et al. WO2002/051809; Sasikumar et al. WO2005/034947; Devita et al. WO2003/045313; Gillig et al. WO2005/040257; and Schwink et al. WO2004/072025.

MCH has been shown to modulate behaviors and disease states other than hyperphagia and obesity. MCHR1 antagonists have been shown to inhibit behavior in rodents that models depression and anxiety in humans (Hervieu (2003) Expert Opinion on Therapeutic Targets 7(4), 495-511 and references therein; Georgescu et al. (2005) Journal of Neuroscience 25(11), 2933-2940; Chaki et al. (2005) Journal of Pharm. and Exptl. Therapeutics 313, 831-839). These rodent models include forced swim test, vocalization and various models of social interaction. Recent studies also support a role of MCHR1 in cognition (Adamantidis et al. (2005) European Journal of Neuroscience 21, 2837-2844).

There is still a need for selective MCH receptor antagonists in order to address the role of the MCH receptor in food intake and regulation of body weight. Unlike a number of existing medications for weight loss, it is believed that a selective MCH receptor antagonist would provide a means of safely reducing food intake and body weight in humans. Such selective MCH receptor antagonists would be useful for the treatment of, for example, obesity, hyperphagia, anxiety, depression and related disorders.

SUMMARY OF THE INVENTION

In one embodiment of the present invention, provided is a compound of the formula (I):

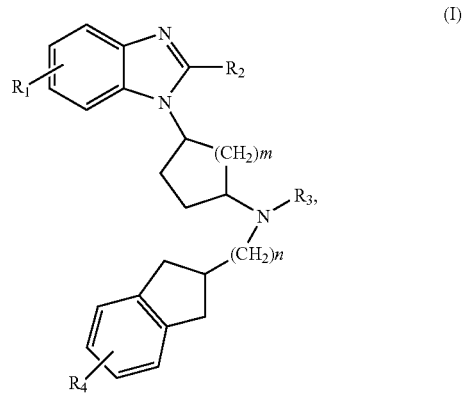

wherein:
$R_1$ is hydrogen, lower alkyl, halo or cyano;
$R_2$ is hydrogen, lower alkyl, alkoxy or hydroxyalkyl;

$R_3$ is hydrogen, lower alkyl, lower alkyl carbonyl or aryl;
$R_4$ is hydrogen, lower alkyl, halo, lower alkylhalo or cyano;
m is 1 or 2; and
n is 0 or 1, and pharmaceutically acceptable salts thereof.

In another embodiment of the present invention, provided is a pharmaceutical composition comprising a therapeutically effective amount of a compound according to formula (I) or a pharmaceutically acceptable salt thereof, and a pharmaceutically acceptable carrier.

In a further embodiment of the present invention, provided is method for treating obesity in a patient in need of such treatment, comprising administering a therapeutically effective amount of a compound according to formula (I) or a pharmaceutically acceptable salt thereof to a patient in need thereof.

DETAILED DESCRIPTION OF THE INVENTION

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl" means, for example, a branched or unbranched, cyclic or acyclic, saturated or unsaturated (e.g. alkenyl or alkynyl)hydrocarbyl group which may be substituted or unsubstituted. Where cyclic, the alkyl group is preferably $C_3$ to $C_{12}$, more preferably $C_4$ to $C_{10}$, more preferably $C_4$ to $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and isopentyl), more preferably methyl. It will be appreciated therefore that the term "alkyl" as used herein includes alkyl (branched or unbranched), substituted alkyl (branched or unbranched), alkenyl (branched or unbranched), substituted alkenyl (branched or unbranched), alkynyl (branched or unbranched), substituted alkynyl (branched or unbranched), cycloalkyl, substituted cycloalkyl, cycloalkenyl, substituted cycloalkenyl, cycloalkynyl and substituted cycloalkynyl.

As used herein, the term "lower alkyl" means, for example, a branched or unbranched, cyclic or acyclic, saturated or unsaturated (e.g. alkenyl or alkynyl) hydrocarbyl group wherein said cyclic lower alkyl group is $C_3$, $C_4$, $C_5$, $C_6$ or $C_7$, and wherein said acyclic lower alkyl group is $C_1$, $C_2$, $C_3$, $C_4$, $C_5$, or $C_6$, preferably from 1 to 4 carbon atoms. Typical lower alkyl groups include methyl, ethyl, propyl (n-propyl or isopropyl), butyl (n-butyl, isobutyl or tertiary-butyl), pentyl and hexyl. It will be appreciated therefore that the term "lower alkyl" as used herein includes, for example, lower alkyl (branched or unbranched), lower alkenyl (branched or unbranched), lower alkynyl (branched or unbranched), cycloloweralkyl, and cycloloweralkynyl. When attached to another functional group, lower alkyl as used herein may be divalent, e.g., —lower alkyl-COOH.

As used herein, the term "aryl" means, for example, a substituted or unsubstituted carbocyclic aromatic group, such as phenyl or naphthyl, or a substituted or unsubstituted heteroaromatic group containing one or more, preferably one, heteroatom, such as pyridyl, pyrrolyl, furanyl, thienyl, thiazolyl, isothiazolyl, oxazolyl, isoxazolyl, oxadiazolyl, thiadiazolyl pyrazolyl, imidazolyl, triazolyl, pyrimidinyl pyridazinyl, pyrazinyl, triazinyl, indolyl, indazolyl, quinolyl, quinazolyl, benzimidazolyl, benzothiazolyl, benzisoxazolyl and benzisothiazolyl.

The alkyl and aryl groups may be substituted or unsubstituted. Where substituted, there will generally be, for example, 1 to 3 substituents present, preferably 1 substituent. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylaminocarbonyloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl); and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxindolyl, isoindolyl, indazolyl, indolinyl, 7-azaindolyl, benzopyranyl, coumarinyl, isocumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The lower alkyl groups may be substituted or unsubstituted, preferably unsubstituted. Where substituted, there will generally be, for example, 1 to 3 substitutents present, preferably 1 substituent.

As used herein, the term "alkoxy" means, for example, alkyl-O— and "alkoyl" means, for example, alkyl-CO—. Alkoxy substituent groups or alkoxy-containing substituent groups may be substituted by, for example, one or more alkyl groups.

As used herein, the term "halogen" means a fluorine, chlorine, bromine or iodine atom, preferably a fluorine, chlorine or bromine atom, and more preferably a fluorine or chlorine atom.

"Pharmaceutically acceptable," such as pharmaceutically acceptable carrier, excipient, etc., means pharmacologically acceptable and substantially non-toxic to the subject to whom the particular compound is administered.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a well known technique which is used in attempting to improve properties involving physical or chemical stability, e.g., hygroscopicity, flowability or solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid. Examples of ester groups which are cleaved (in this case hydrolyzed) in vivo to the corresponding carboxylic acids are those in which the cleaved hydrogen is replaced with -lower alkyl which is optionally substituted, e.g., with heterocycle, cycloalkyl, etc. Examples of substituted lower alkyl esters are those in which -lower alkyl is substituted with pyrrolidine, piperidine, morpholine, N-methylpiperazine, etc. The group which is cleaved in vivo may be, for example, ethyl, morpholino ethyl, and diethylamino ethyl. In connection with the present invention, —$CONH_2$ is also considered an ester, as the —$NH_2$ is cleaved in vivo and replaced with a hydroxy group, to form the corresponding carboxylic acid.

Further information concerning examples of and the use of esters for the delivery of pharmaceutical compounds is available in Design of Prodrugs. Bundgaard H. ed. (Elsevier, 1985). See also, H. Ansel et. al., Pharmaceutical Dosage Forms and Drug Delivery Systems (6th Ed. 1995) at pp. 108-109; Krogsgaard-Larsen, et. al., Textbook of Drug Design and Development (2d Ed. 1996) at pp. 152-191.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. The therapeutically effective amount of the compounds of formula I can vary within wide limits depending on the disease to be controlled, the age and the individual condition of the patient and the mode of administration, and will, of course, be fitted to the individual requirements in each particular case. Preferably, the therapeutically effective amount may be from about 0.01 mg/kg to about 50 mg/kg per day, more preferably from about 0.3 mg/kg to about 10 mg/kg per day.

The daily dosage can be administered as a single dose or in divided doses, or for parenteral administration it may be given as continuous infusion.

Compounds of the present invention can be prepared beginning with commercially available starting materials and utilizing general synthetic techniques and procedures known to those skilled in the art. Outlined below are preferred reaction schemes suitable for preparing such compounds.

Further exemplification is found in the specific Examples detailed below.

Scheme 1: General method of preparing substituted indan-2-carbaldehyde

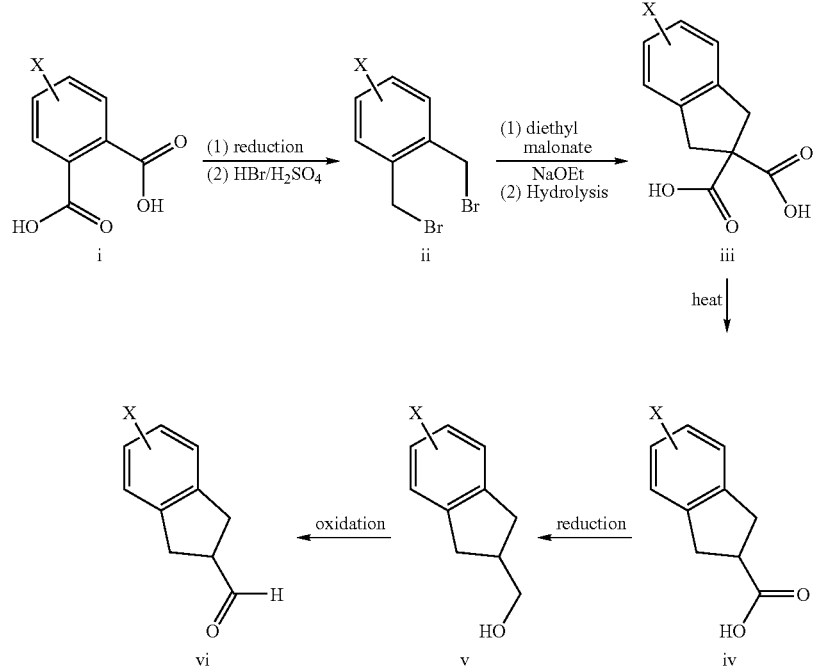

The substituted indan-2-carbaldehyde can be prepared from the corresponding carboxylic acid through reduction and oxidation reactions. The indan-2-carboxylic acid can be prepared with a similar method to literature example (*J. Med. Chem.* 1989, 38, 1988-1996). The substituted benzene dicarboxylic acid i (X=H, F, Br, Cl, $CF_3$) can be reduced to a diol which can be converted to dibromide ii. Alkylation of diethyl malonate with the dibromide ii followed by saponification can provide indan-2,2-dicarboxylic acid iii, which can be decarboxylated to produce substituted indan-2-carboxylic acids iv. The indan-2-carboxylic acid iv can be reduced to a corresponding alcohol v, which can be oxidized to generate the desired substituted indan-2-carbaldehyde vi.

The chiral 5-bromo-indan-2-carboxylic acid (iv where X=5-Br) can be prepared from the corresponding indene through an asymmetric catalytic hydrogenation with a similar method to literature example (U.S. Pat. No. 5,936,000) to generate both (R) and (S)-enantiomers. Conversion of bromide (v where X=5-Br) to cyanide (v where X=5-CN) can be accomplished through palladium catalyzed ligand exchange reactions by using zinc cyanide and $Pd(PPh_3)_4$.

Scheme 2: Method of preparing 4-benzoimidazol-1-yl-cyclohexylamine

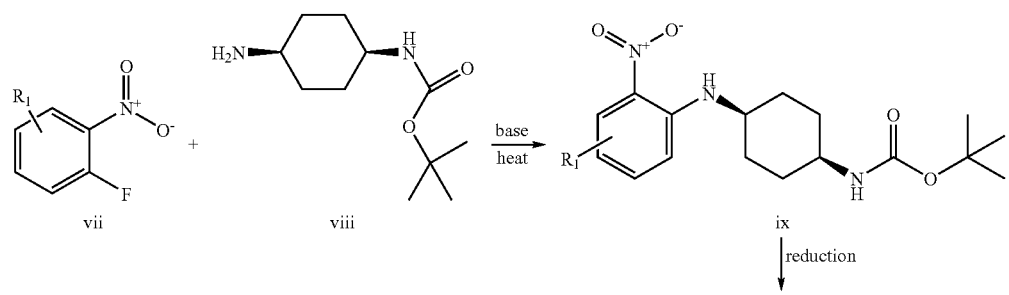

-continued

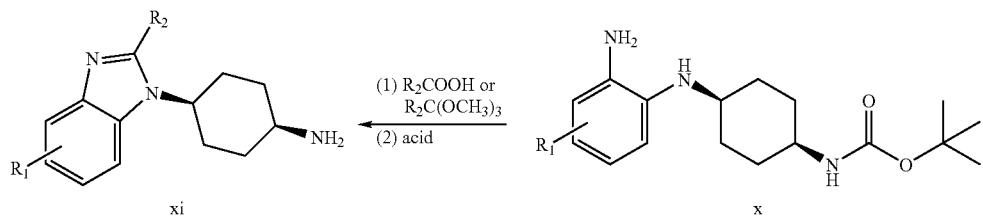

The 4-benzoimidazol-1-yl-cyclohexylamine can be prepared by reacting N-Boc-1,4-cyclohexyldiamine viii with substituted fluoro-nitrobenzene vii ($R_1$ can be H, $CH_3$, F, Cl, CN, etc) to provide the N-aryl compound ix. The nitro group in compound ix can be reduced to the corresponding phenylenediamine x. The reaction of phenylenediamine x with carboxylic acid under acidic condition will form the desired benzoimidazole xi. Alternatively, the ring cyclization can be performed by reacting compound x with trimethyl orthocarboxylate to generate the desired benzoimidazole which can be deprotected under acidic condition to provide compound xi.

The same method described in Scheme 2 can be applied to larger or smaller ring systems other than the cyclohexane, and the nitrogen linkage to cycloalkane can be cis- or trans-configuration.

Scheme 3: Coupling of cyclohexylamine with indan-2-carbaldehyde

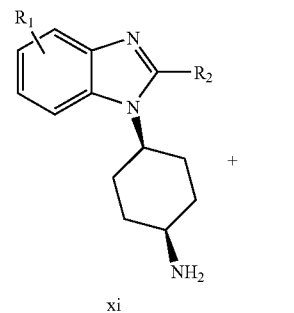

-continued

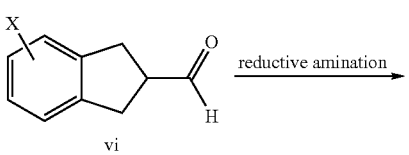

The coupling of 4-benzoimidazol-1-yl-cyclohexylamine xi with the indan-2-carbaldehyde vi can be accomplished through a reductive amination reaction by using $NaCNBH_3$ or $NaBH(OAc)_3$ to generate the indane derived amine xii. The diaminocycloalkane can be cis- or trans-configuration. The same method can be applied to other ring systems.

Scheme 4: Alternative method of coupling indane with benzoimidazole

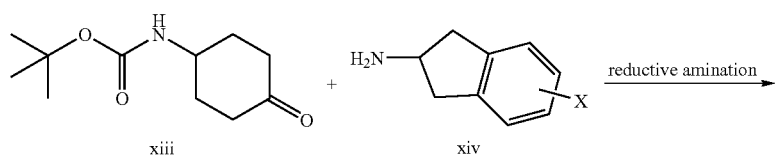

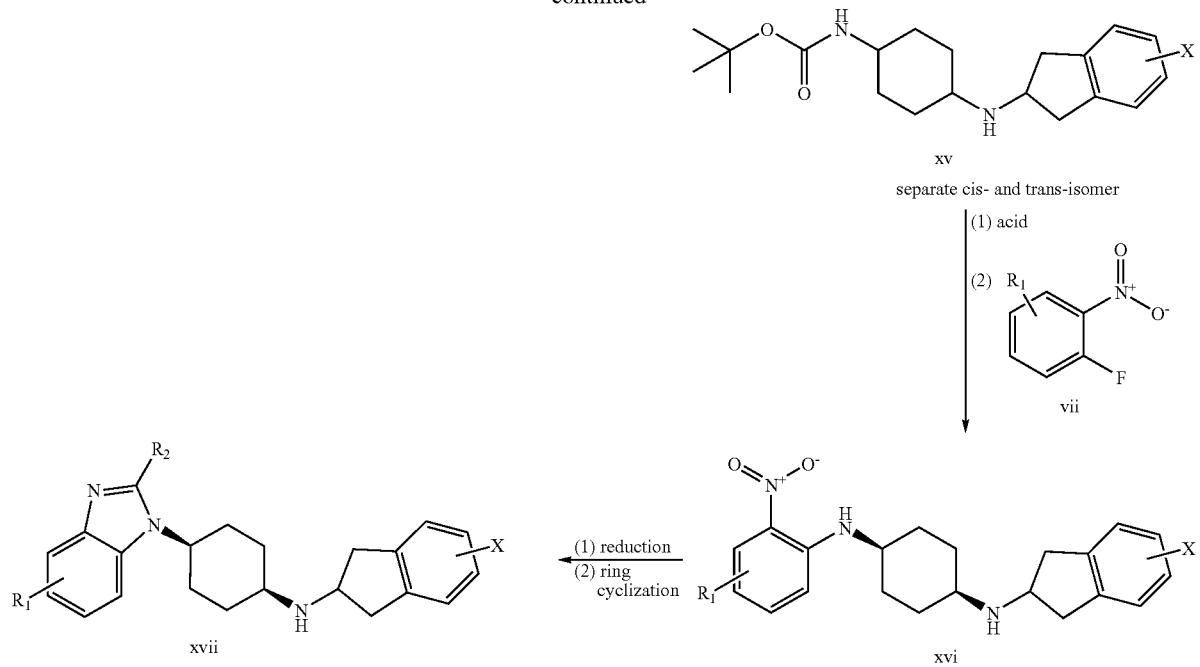

Alternatively, the aminoindane xiv (prepared from indan-2-carboxylic acid iv through Curtius rearrangement) can be coupled to N-Boc-4-aminocyclohexanone xiii through reductive amination to generate cis- and trans-isomers xv which can be separated. Following the removal of the N-Boc group and nucleophilic aromatic substitution with fluoro-nitrobenzene vii, the indane-derived benzoimidazole xvii can be prepared through reduction and ring cyclization reactions using the same method described in Scheme 2.

EXAMPLES

Part I

Preparation of Preferred Intermediates trans-3-(2,5-Dimethyl-benzoimidazol-1-yl)-cyclopentylamine; hydrochloride

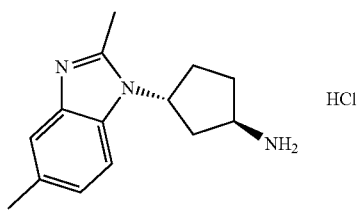

To a stirred solution of 1,3-cyclopropanediol (5 g, 49 mmol) and imidazole (5 g, 73.4 mmol) in DMF (20 mL) was added t-butyldimethylsilyl chloride (5.2 g, 34.5 mmol) and the mixture was stirred for 90 minutes at room temperature. The mixture was diluted with brine (200 mL) and extracted with ether three times (1×100 mL and 2×50 mL). Each extract was washed with a portion of brine. The organic phases were combined, dried over sodium sulfate and evaporated to dryness. The mixture of cis/trans isomers was purified by column chromatography using ether and hexanes to give the predominant trans-3-(tert-butyl-dimethyl-silanyloxy)-cyclopentanol as a colorless liquid (4.1 g).

The trans-3-(tert-butyl-dimethyl-silanyloxy)-cyclopentanol (1.08 g, 5 mmol) was combined with triphenylphosphine (1.44 g, 5.49 mmol) in dry THF (25 mL) and the stirring solution was chilled to 0° C. Diethyl azodicarboxylate (DEAD, 960 mg, 5.51 mmol) was added over 5 minutes. The mixture was stirred for 5 minutes and diphenylphosphoryl azide (DPPA, 1.185 mL, 5.49 mmol) was added over 5 minutes. The resulting mixture was stirred for 17 hours at room temperature. The reaction mixture was evaporated to a small volume and partitioned with ether (100 mL) and water (50 mL). The organic layer was dried over sodium sulfate, filtered and evaporated. The residue was purified by flash column chromatography eluting with ether and hexane mixtures to produce cis-3-(azido-cyclopentyloxy)-tert-butyl-dimethyl-silane as pale yellow oil (930 mg).

The cis-3-(azido-cyclopentyloxy)-tert-butyl-dimethyl-silane (930 mg, 3.85 mmol) was dissolved in ethanol (10 mL) and treated with platinum (IV) oxide monohydrate (100 mg). The mixture was stirred at room temperature under 1 atmosphere of hydrogen for 90 minutes and then filtered through Celite. Solvent was evaporated to give cis-3-(tert-butyl-dimethyl-silanyloxy)-cyclopentylamine as a colorless oil (500 mg). LRMS: calcd for $C_{11}H_{25}NOSi$ (m/e) 215.1705, obsd 216.1 (M+H).

The cis-3-(tert-butyl-dimethyl-silanyloxy)-cyclopentylamine (500 mg, 2.32 mmol) was dissolved in THF (10 mL) and di-tert-butyl dicarbonate (610 mg, 2.79 mmol) was added. The mixture was stirred for 4 hours and solvents were evaporated. The residue was purified by chromatography on silica gel eluting with mixtures of ethyl ether and hexanes to afford cis-3-(tert-butyl-dimethyl-silanyloxy)-cyclopentyl]-carbamic acid tert-butyl ester as an oil (520 mg).

The above cis-3-(tert-butyl-dimethyl-silanyloxy)-cyclopentyl]-carbamic acid tert-butyl ester (1.43 g, 4.5 mmol) was dissolved in acetonitrile (35 mL). To this solution was added 5% aqueous hydrogen fluoride (2.0 mL) and the mixture was stirred for 19 hours at room temperature in a Nalgene bottle. The mixture was treated carefully with a suspension of sodium bicarbonate (1 g) in water (2 mL). Volatiles were removed under reduced pressure at 30° C. The remainder was partitioned between brine (50 mL) and ethyl ether (50 mL). The aqueous phase was further extracted with ethyl ether (2×50 mL). Each extract was washed with a portion of brine. The extracts were combined, dried over sodium sulfate, filtered and the filtrate was evaporated to provide cis-(3-hydroxy-cyclopentyl)-carbamic acid tert-butyl ester as colorless oil (850 mg).

To a stirring solution of cis-(3-hydroxy-cyclopentyl)-carbamic acid tert-butyl ester (850 mg, 4.22 mmol) and triphenylphosphine (1.53 g, 5.83 mmol) in THF (25 mL) cooled to 2° C. was added DEAD reagent (0.92 mL, 5.84 mol) over 5 minutes. The mixture was stirred for 5 minutes and DPPA (1.26 mL, 5.84 mmol) was added over 5 minutes. Stirring was continued for 17 hours at room temperature. The mixture was evaporated to dryness. The residue was stirred in ethyl ether briefly and the white solid triphenylphosphine oxide was removed by filtration (1 g). The filtrate was again reduced in volume and purified by silica gel chromatography eluting with ethyl acetate and hexanes to afford trans-(3-azido-cyclopentyl)-carbamic acid tert-butyl ester (950 mg).

The carbamic acid tert-butyl ester (500 mg, 2.2 mmol) prepared above was dissolved in 20 mL of ethyl alcohol and THF (1:1). The solution was stirred at room temperature under one atmospheric of hydrogen in the presence of $PtO_2$ (50 mg) for 90 minutes. The mixture was filtered and the filtrate was evaporated to provide trans-(3-amino-cyclopentyl)-carbamic acid tert-butyl ester as a white solid (440 mg).

The trans-(3-amino-cyclopentyl)-carbamic acid tert-butyl ester (420 mg, 2.09 mmol) was mixed with 4-fluoro-3-nitrotoluene (342 mg, 2.2 mmol) and potassium carbonate (915 mg, 6.6 mmol) in DMF (20 mL). The stirring mixture was heated at 85° C. for 16.5 hours. The reaction mixture was evaporated under reduced pressure. The residue was partitioned with 50 mL of dichloromethane and 50 mL of brine. The aqueous phase was extracted again with 50 mL of dichloromethane and each organic extract was washed with a portion of brine. After drying, filtering and evaporation of solvents, the crude mixture was purified on silica gel eluting with ethyl acetate and hexanes to give trans-[3-(4-methyl-2-nitrophenylamino)-cyclopentyl]-carbamic acid tert-butyl ester as a orange oil (305 mg). $^1$H-NMR is consistent with the assigned structure. LC-MS showed a single peak, $C_{17}H_{25}N_3O_4$ (m/e) calcd 335.1845, obsd 336.2 (M+1).

The trans-[3-(4-methyl-2-nitro-phenylamino)-cyclopentyl]-carbamic acid tert-butyl ester (320 mg, 0.95 mmol) and palladium on charcoal (10% Pd on carbon, 35 mg) in methanol (15 mL) were shaken at 52 psi of hydrogen pressure for 2.5 hours. The mixture was filtered through Celite®. Solvents were evaporated to yield trans-[3-(2-amino-4-methyl-phenylamino)-cyclopentyl]-carbamic acid tert-butyl ester as a pale brown oil (290 mg). This material (290 mg, 0.95 mmol) was dissolved in a solution (5 mL) of acetic acid and trimethyl orthoacetate (4:1 v/v). The mixture was stirred at 70° C. for 60 minutes and solvents were evaporated. The residue was extracted with ethyl acetate (25 mL) and saturated aqueous sodium bicarbonate (20 mL). The aqueous phase was again extracted with a portion of ethyl acetate and each organic phase was washed with brine. The extracts were combined, dried over sodium sulfate, filtered and evaporated to give trans-[3-(2,5-dimethyl-benzoimidazol-1-yl)-cyclopentyl]-carbamic acid tert-butyl ester as a light brown foam (320 mg). $^1$H-NMR is consistent with the assigned structure. LC-MS showed a single peak, $C_{19}H_{27}N_3O_2$ (m/e) calcd 329.2103, obsd 330.2 (M+H).

The trans-[3-(2,5-dimethyl-benzoimidazol-1-yl)-cyclopentyl]-carbamic acid tert-butyl ester prepared above (320 mg, 0.95 mmol) was dissolved in HCl (4M) in dioxane (5.0 mL) and the solution was stirred for 15 minutes. Solids came out of solution and 1 mL of methanol was added to dissolve the precipitate. Stirring was continued for 60 minutes and the reaction mixture was evaporated to a sticky solid which was stirred with ethyl ether. The resulting solid was filtered to provide trans-3-(2,5-dimethyl-benzoimidazol-1-yl)-cyclopentylamine hydrochloride salt as an off white powder (250 mg). LR-MS calcd for $C_{14}H_{19}N_3$ (m/e) 229.1579, obsd 230.2 (M+H).

cis-3-(2,5-Dimethyl-benzoimidazol-1-yl)-cyclopentylamine

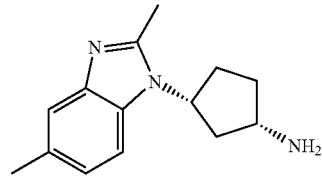

To a solution of cis-(3-hydroxy-cyclopentyl)-carbamic acid tert-butyl ester (750 mg, 3.72 mmol, prepared in previous intermediate) in THF (20 mL) at 2° C. was added triphenylphosphine (1.1 g, 4.19 mmol) and diethyl azodicarboxylate (0.7 mL, 4.4 mmol). The solution was stirred for 10 minutes. Acetic acid (0.6 mL, 10.48 mmol) in THF (5 mL) was added over 2 minutes and the mixture was first stirred at 2° C. for 20 minutes and then at room temperature for 3 hours. The mixture was evaporated to dryness and the residue was stirred with ethyl ether (20 mL). The resulting solid was removed by filtration. The filtrate was evaporated and the residue was purified by flash column chromatography eluting with ethyl ether and hexane to produce acetic acid trans-3-tert-butoxycarbonylamino-cyclopentyl esters a white solid (453 mg).

The ester prepared above (430 mg, 1.76 mmol) was dissolved in THF (1 mL) and methanol (1 mL). To this solution was added 4N aqueous sodium hydroxide solution (1 mL) and the solution was stirred for 60 minutes at room temperature. Solvents were evaporated and the residue was partitioned with dichloromethane (25 mL) and brine (25 mL). The aqueous phase was further extracted with dichloromethane (25 mL). The organic extract was washed with brine and dried over sodium sulfate. Solvents were evaporated to give trans-(3-hydroxy-cyclopentyl)-carbamic acid tert-butyl ester as a white solid (350 mg).

The trans-(3-hydroxy-cyclopentyl)-carbamic acid tert-butyl ester was converted to cis-(3-amino-cyclopentyl)-carbamic acid tert-butyl ester using the same method described previously. The resulting compound was further converted to cis-[3-(2,5-dimethyl-benzoimidazol-1-yl)-cyclopentyl]-carbamic acid tert-butyl ester using the same method described in the preparation of the hydrochloride salt of trans-3-(2,5-dimethyl-benzoimidazol-1-yl)-cyclopentylamine. After the acid cleavage of the carbamic acid tert-butyl ester and base extraction, cis-3-(2,5-dimethyl-benzoimidazol-1-yl)-cyclopentylamine was obtained as pale brown oil. LR-MS calcd for $C_{14}H_{19}N_3$ (m/e) 229.1579, obsd 230.2 (M+H).

cis-4-(2,5-Dimethyl-benzoimidazol-1-yl)-cyclohexylamine; hydrochloride

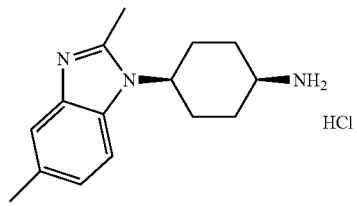

To a mixture of tert-butyl cis-4-aminocyclohexanecarbamate (1.27 g, 5.93 mmol) and 4-fluoro-3-nitrotoluene (0.92 g, 5.93 mmol) in DMF (20 mL) was added potassium carbonate (1.64 g, 11.88 mmol). The mixture was heated at 85° C. and stirred overnight. The mixture was cooled to room temperature and the solid was filtered. The filtrate was evaporated to dryness. The residue was extracted with ethyl acetate and brine. The organic layer was dried over sodium sulfate and solvents were evaporated. The resulting material was purified through flash column chromatography using hexanes and ethyl acetate (4:1) to give an orange colored solid as cis-[4-(4-methyl-2-nitro-phenylamino)-cyclohexyl]-carbamic acid tert-butyl ester (1.88 g). This material (1.80 g, 5.17 mmol) was suspended in a mixture of methanol (50 mL) and water (25 mL). To this suspension was added ammonium chloride (4.15 g, 77.6 mmol) and zinc dust (3.36 g, 51.6 mmol). The mixture was stirred at room temperature for 20 minutes and THF (20 mL) was added. The mixture was stirred an additional 1 hr during which the orange color disappeared. The mixture was filtered and rinsed with THF and ethyl acetate. The filtrate was extracted with brine and ethyl acetate. Solvents were evaporated to give cis-[4-(2-amino-4-methyl-phenylamino)-cyclohexyl]-carbamic acid tert-butyl ester (1.65 g). LC-MS showed a single peak, $C_{18}H_{29}N_3O_2$ (m/e) calcd 319.2260, obsd 320.3 (M+H).

The above compound (850 mg, 2.65 mmol) was mixed with acetic acid (8 mL) and trimethyl orthoacetate (2 mL). The mixture was heated at 65° C. for 2 hrs. Solvents were evaporated and the residue was extracted with ethyl acetate and sodium bicarbonate solution. The organic layer was dried over sodium sulfate and solvents were evaporated to give a pale brown solid as cis-[4-(2,5-dimethyl-benzoimidazol-1-yl)-cyclohexyl]-carbamic acid tert-butyl ester. This solid was dissolved in methylene chloride (3 mL) and trifluoroacetic acid (3 mL) was added. The mixture was stirred at room temperature for 2 hrs. Solvents were evaporated and the residue was dissolved in methylene chloride (4 mL). To this solution was added gaseous hydrogen chloride in dioxane (4M, 4 mL). Solvents were evaporated and the residue was triturated with ether. Solids were filtered and washed with ether to give a hydrochloride salt of cis-4-(2,5-dimethyl-benzoimidazol-1-yl)-cyclohexylamine (630 mg). LC-MS showed a single peak, $C_{15}H_{21}N_3$ (m/e) calcd 243.1735, obsd 244.2 (M+H).

cis-4-(5-Fluoro-2-methyl-benzoimidazol-1-yl)-cyclohexylamine; hydrochloride

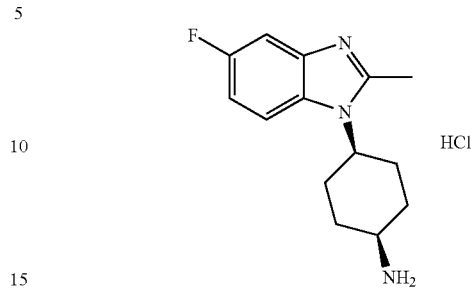

This compound was prepared with the same method as the preparation of cis-4-(2,5-dimethyl-benzoimidazol-1-yl)-cyclohexylamine described previously. $^1$H-NMR (DMSO-$d_6$) ☐ 8.75 (dd, 1H), 8.56 (br s, 3H), 7.66 (dd, 1H), 7.38 (dt, 1H), 4.57 (t, 1H), 3.47 (br s, 1H), 2.89 (s, 3H), 2.38 (m, 2H), 1.88-2.09 (m, 6H).

cis-1-(4-Amino-cyclohexyl)-2-methyl-1H-benzoimidazole-5-carbonitrile; hydrochloride

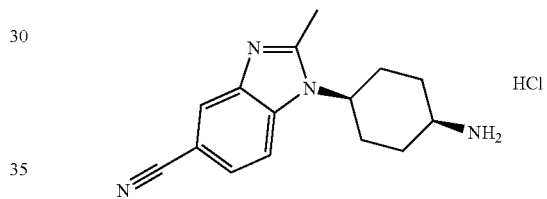

This compound was prepared with the same method as the preparation of cis-4-(2,5-dimethyl-benzoimidazol-1-yl)-cyclohexylamine described previously. $^1$H-NMR (DMSO-$d_6$) ☐ 8.63 (d, 1H), 8.42 (br s, 3H), 8.24 (s, 1H), 7.77 (d, 1H), 4.47 (t, 1H), 3.48 (br s, 1H), 2.80 (s, 3H), 2.38 (m, 2H), 2.00 (m, 4H), 1.84 (br d, 2H).

cis-2-[1-(4-Amino-cyclohexyl)-5-chloro-1H-benzoimidazol-2-yl]-propan-2-ol; hydrochloride

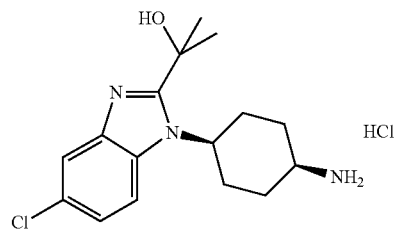

To a mixture of cis-[4-(2-amino-4-chloro-phenylamino)-cyclohexyl]-carbamic acid tert-butyl ester (1.25 g, 3.67 mmol, prepared from 1-chloro-4-fluoro-3-nitrobenzene and tert-butyl cis-4-aminocyclohexanecarbamate) and 2-hydroxyisobutyric acid (2.7 g, 25.9 mmol) in water (5 mL) was added concentrated hydrochloric acid (3.25 mL, 40 mmol). The mixture was stirred and heated at 110° C. for 2 days. The dark colored solution was treated with ammonium hydroxide (15 mL, 225 mmol) and extracted with methylene chloride. The organic layer was washed with brine and dried over sodium sulfate. After the evaporation of solvents, a red colored solid was obtained (1.1 g). This material was dissolved in THF (20 mL) and treated with di-tert-butyl-dicarbonate (950 mg, 4.3 mmol). The mixture was stirred at room temperature overnight. Solvents were evaporated and the residue was purified through flash column chromatography using ethyl acetate and hexanes (1:4) to give [4-(5-chloro-2-(1-hydroxy-1-methyl-ethyl)-benzoimidazol-1-yl)-cyclohexyl]-carbamic acid tert-butyl ester (600 mg). This compound was dissolved in methylene chloride (4 mL) and trifluoroacetic acid (1 mL) was added. The solution was stirred at room temperature for 1 hr. Solvents were evaporated and the residue was extracted with methylene chloride and sodium hydroxide solution (1N). The organic layer was dried over sodium sulfate and solvents were evaporated. The residue was dissolved in methylene chloride and treated with hydrogen chloride in dioxane (4M). Solvents were evaporated and the residue was triturated with ether. The purple solid was filtered to give a hydrochloride salt of cis-2-[1-(4-amino-cyclohexyl)-5-chloro-1H-benzoimidazol-2-yl]-propan-2-ol. $^1$H-NMR (CD$_3$OD) □ 7.96 (d, 1H), 7.57 (s, 1H), 7.21 (d, 1H), 5.34 (m, 1H), 2.61 (m, 2H), 1.72-1.89 (m, 13H).

A minor product of trans-isomer was also isolated from the condensation of the cis-[4-(2-amino-4-chloro-phenylamino)-cyclohexyl]-carbamic acid tert-butyl ester with 2-hydroxy-isobutyric acid. Using the same method, the trans-isomer was converted to trans-2-[1-(4-amino-cyclohexyl)-5-chloro-1H-benzoimidazol-2-yl]-propan-2-ol.

cis/trans-2-[1-(4-Amino-cyclohexyl)-5-methyl-1H-benzoimidazol-2-yl]-propan-2-ol; hydrochloride

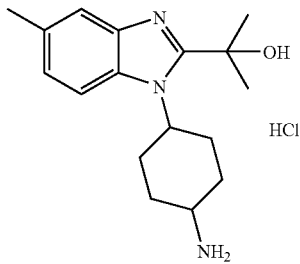

This compound was prepared with the same method as the preparation of 2-[1-(4-amino-cyclohexyl)-5-chloro-1H-benzoimidazol-2-yl]-propan-2-ol described previously. $^1$H-NMR indicated a mixture of cis/trans-isomer. LC-MS calcd for C$_{17}$H$_{25}$N$_3$O (m/e) 287.1998, obsd 288.2 (M+H).

5-Trifluoromethyl-indan-2-carbaldehyde

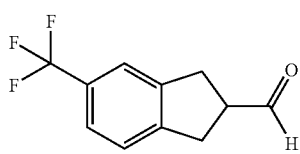

To a solution of 4-trifluoromethylbenzene-1,2-dicarboxylic acid (5.85 g, 25 mmol) in THF (50 mL) at −78° C. was added borane in THF (1.0 M, 75 mL) and the mixture was stirred for 10 minutes. The mixture was then allowed to warm to room temperature and stirred overnight. Methanol (30 mL) was added and solvents were evaporated. The mixture was partitioned between ether and aqueous hydrochloric acid (1N). The organic layer was washed with brine and concentrated sodium bicarbonate solution. After the evaporation of solvents, colorless oil was obtained as (2-hydroxymethyl-4-trifluoromethyl-phenyl)-methanol (5.15 g). $^1$H-NMR (CDCl$_3$) □ 7.58 (m, 2H), 7.51 (s 1H), 4.79 (s, 4H), 2.88 (m, 2H).

The above diol (5.15 g, 25 mmol) was suspended in aqueous hydrobromic acid (48%, 100 mL) containing concentrated sulfuric acid (1 mL). The mixture was refluxed for 15 hrs. The solution was extracted with petroleum ether (150 mL) and ether (75 mL). The organic layer was washed with water and brine and dried over sodium sulfate. Solvents were evaporated to give a brown oil as 1,2-bis-bromomethyl-4-trifluoromethylbenzene (7.72 g). $^1$H-NMR (CDCl$_3$) □ 7.62 (s, 1H), 7.58 (d, 1H), 7.54 (d, 1H), 4.66 (s, 4H).

Sodium (1.12 g, 48.6 mmol) was added to ethanol (16 mL). The solution was heated to reflux until all sodium was dissolved. To this solution was added diethyl malonate (3.71 g, 23.19 mmol) in ether (45 mL) and the above 1,2-bis-bromomethyl-4-trifluoromethylbenzene (7.7 g, 23.19 mmol) in ether (45 mL). The mixture was refluxed for 16 hrs and the precipitate was filtered out. The filtrate was evaporated and the residue was treated with water (35 mL) and potassium hydroxide (5.30 g). The mixture was stirred and refluxed for 5 hrs and treated with water (20 mL). The resulting mixture was extracted with ether (50 mL). The aqueous phase was acidified with concentrated hydrochloric acid and cooled in an ice bath. Solids were filtered and washed with water. After air drying, 5-trifluoromethyl-indan-2,2-dicarboxylic acid was obtained (3.08 g). LC-MS showed a single peak, C$_{12}$H$_{19}$F$_3$O$_4$ (m/e) calcd 274.0453, obsd 273.0 (M−H).

The above dicarboxylic acid (3.07 g, 11.2 mmol) was heated to 200° C. until evolution of gas ceased. The oily material was heated at 200° C. for 15 more minutes and cooled down to room temperature. This material was refluxed in hexanes (100 mL) and insoluble material removed by filtration. The filtrate was evaporated to give a solid as 5-trifluoromethyl-indan-2-carboxylic acid (2.49 g). LC-MS showed a single peak, C$_{11}$H$_9$F$_3$O$_2$ (m/e) calcd 230.0555, obsd 229.0 (M−H). $^1$H-NMR (CDCl$_3$) □ 7.47 (s, 1H), 7.44 (d, 1H), 7.31 (d, 1H), 3.44 (m, 1H), 3.33 (m, 4H).

The above 5-trifluoromethyl-indan-2-carboxylic acid (1.03 g, 4.47 mmol) was dissolved in THF (25 mL) and cooled to 0° C. To this solution was added a solution of borane in THF (1M, 6.5 mL). The mixture was warmed to room temperature and stirred for 1 hr. The mixture was treated with water (5 mL) and solvents were evaporated. The residue was extracted with ether and hydrochloric acid (1M). The organic phase was washed with brine and sodium bicarbonate solution. The ether solution was dried and solvents were evaporated to give oily material as 5-trifluoromethyl-indan-2-yl-methanol (0.98 g).

The above 5-trifluoromethyl-indan-2-yl-methanol (216 mg, 1 mmol) was dissolved in methylene chloride (15 mL) and the solution was cooled in an ice bath. To this solution was added Dess-Martin reagent (450 mg, 1.06 mmol) in four portions. The mixture was warmed to room temperature and stirred for 1 hr. The mixture was evaporated to dryness and the residue was triturated with petroleum ether (14 mL) and ether (7 mL). The precipitate was filtered out and the filtrate was extracted with ether and sodium bicarbonate solution. The organic layer was dried over sodium sulfate and solvents were evaporated to give 5-trifluoromethyl-indan-2-carbaldehyde (210 mg) as pale green oil. $^1$H-NMR (CDCl$_3$) ☐ 9.78 (s, 1H), 7.48 (s, 1H), 7.43 (d, 1H), 7.32 (d, 1H), 3.33-3.38 (m, 3H), 3.15-3.27 (m, 2H).

Part II

Preparation of Preferred Compounds

Example 1 cis-4-(2,5-Dimethyl-benzoimidazol-1-yl)-cyclohexyl]-indan-2-yl-amine; hydrochloride

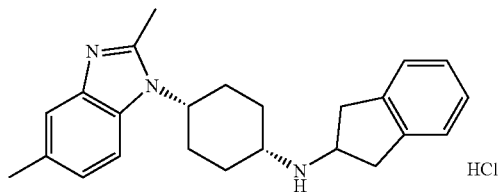

Sodium cyanoborohydride (590 mg, 9.39 mmol) was added to a solution of Boc-4-aminocyclohexanone (1.00 g, 4.69 mmol) and 2-aminoindane hydrochloride (955 mg, 5.63 mmol) in ethanol (25 mL). After stirring for 16 h, the reaction mixture was poured into aqueous 1.0M sodium hydroxide solution (75 mL) and extracted three times with ethyl acetate. The combined organic layers were washed with brine and dried over sodium sulfate. Filtration followed by removal of volatiles under reduced pressure afforded a gummy solid. Flash chromatography (0-5% methanol in ethyl acetate) provided (in order of elution): cis-[4-(indan-2-ylamino)-cyclohexyl]-carbamic acid tert-butyl ester (700 mg; 45%) and trans-[4-(indan-2-ylamino)-cyclohexyl]-carbamic acid tert-butyl ester (300 mg; 19%) as gummy solids.

cis-[4-(Indan-2-ylamino)-cyclohexyl]-carbamic acid tert-butyl ester (315 mg; 0.95 mmol) was added to 2M hydrogen chloride in dioxane and methanol (1:1, 6 mL) and the solution was stirred for 1 hr at room temperature. All volatiles were removed under reduced pressure and the resulting foamy solid was partitioned between chloroform and 1M potassium carbonate solution. The aqueous phase was extracted three times with chloroform and the combined organic layers were dried over sodium sulfate. Filtration followed by removal of volatiles under reduced pressure afforded N-indan-2-yl-cyclohexane-1,4-cis-diamine (220 mg).

A mixture of N-indan-2-yl-cyclohexane-1,4-cis-diamine (220 mg, 0.96 mmol), 3-nitro-4-fluorotoluene (225 mg, 1.45 mmol) and potassium carbonate (305 mg, 2.87 mmol) in n-butanol (5 mL) was heated to reflux for 17 h. The reaction mixture was then filtered and all volatiles were removed under reduced pressure. The crude product was purified by flash chromatography (0-10% methanol in chloroform) to yield N-(2-nitro-4-methyl-phenyl)-N'-indan-2-yl-cyclohexane-cis-1,4-diamine as an orange waxy solid (305 mg, 87%).

A mixture of N-(2-nitro-4-methyl-phenyl)-N'-indan-2-yl-cyclohexane-cis-1,4-diamine (300 mg, 0.82 mmol) and 10% Pd on carbon (50 mg) in ethanol (15 mL) were shaken under hydrogen pressure (40 psi) for 90 min. The catalyst was then removed by filtration through Celite® and all volatiles were removed under reduced pressure to yield the product phenylenediamine as a light brown waxy solid (260 mg) which was used without further purification.

The aforementioned phenylenediamine (100 mg, 0.299 mmol) was dissolved in acetic acid (2.8 mL) and trimethyl orthoacetate (0.7 mL) and the solution was heated to 70° C. for 1 h. The reaction mixture was cooled to room temperature and all volatiles were removed under reduced pressure. The residue was suspended in 1.0 M aqueous potassium carbonate and extracted three times with ethyl acetate. The combined organic layers were washed with brine and dried over sodium sulfate. Filtration followed by removal of volatiles under reduced pressure gave brown oil. Purification by flash chromatography (2.5-5% methanol in methylene chloride) gave [cis-4-(2,5-dimethyl-benzoimidazol-1-yl)-cyclohexyl]-indan-2-yl-amine as a foamy solid (85 mg) which was converted to a hydrochloride salt. $^1$H-NMR is consistent with the assigned structure. LRMS calcd for C$_{24}$H$_{29}$N$_3$ (m/e) 359.2361, obsd 360.2 (M+H).

Example 2 trans-(S)-(5-Bomo-indan-2-ylmethyl)-[3-(2,5-dimethyl-benzoimidazol-1-yl)-cyclopentyl]-amine

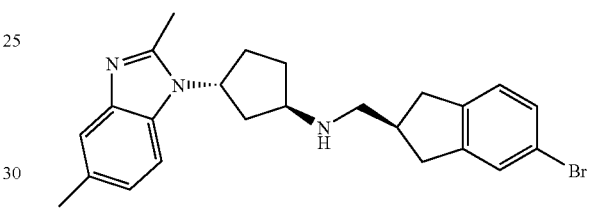

To a solution of trans-3-(2,5-dimethyl-benzoimidazol-1-yl)-cyclopentyl amine hydrochloride (250 mg, 0.47 mmol) and (S)-5-bromo-indan-2-carbaldehyde (113 mg, 0.5 mmol) in methanol (5 mL) containing 5% acetic acid was added a solution of sodium cyanoborohydride (32 mg, 0.509 mmol) in THF (0.5 mL). After stirring for 1 hour, the mixture was evaporated to dryness under reduced pressure and the residue was partitioned with saturated aqueous sodium bicarbonate solution (50 mL) and dichloromethane (3×25 mL). Each extract was washed with brine. Following the drying of the extracts from sodium sulfate, filtration and evaporation, the residue was purified by flash chromatography eluting with ethyl acetate and hexanes in the presence of 4% methanol to afford trans-(S)-(5-bomo-indan-2-ylmethyl)-[3-(2,5-dimethyl-benzoimidazol-1-yl)-cyclopentyl]-amine as an off-white foam (102 mg). $^1$H-NMR is consistent with the assigned structure. LC-MS showed a single peak, C$_{24}$H$_{28}$BrN$_3$ (m/e) calcd 437.1467, obsd 438.1 (M+H).

Example 3 trans-(5-Chloro-indan-2-ylmethyl)-[3-(2,5-dimethyl-benzoimidazol-1-yl)-cyclopentyl]-amine

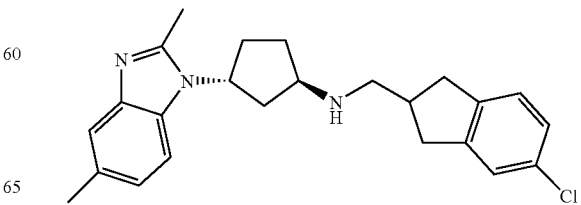

This compound was prepared from trans-3-(2,5-dimethyl-benzoimidazol-1-yl)-cyclopentylamine hydrochloride and 5-chloro-indan-2-carbaldehyde using the same reductive amination method described in previous example. $^1$H-NMR is consistent with the assigned structure. LC-MS showed a single peak, $C_{24}H_{28}ClN_3$ (m/e) calcd 393.1972, obsd 394.2 (M+H).

Example 4 cis-(S)-(5-Bromo-indan-2-ylmethyl)-[4-(2,5-dimethyl-benzoimidazole-1-yl)-cyclohexyl]-amine hydrochloride

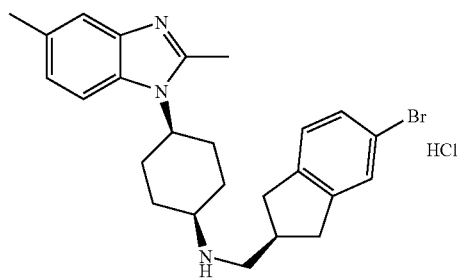

The hydrochloride salt of cis-4-(2,5-dimethyl-benzoimidazol-1-yl)-cyclohexylamine (104.5 mg, 0.33 mmol) was mixed with (S)-5-bromo-indan-2-carbaldehyde (75 mg, 0.33 mmol) in 5 mL of methanol containing 5% acetic acid. The mixture was stirred at room temperature for 10 minutes and sodium cyanoborohydride (20.5 mg, 0.33 mmol) in 0.2 mL of THF was added. The mixture was stirred at room temperature for 3 hours. The mixture was evaporated and the residue was extracted with methylene chloride and concentrated sodium bicarbonate solution. The organic layer was washed with brine and solvents were evaporated. The residue was purified through flash column chromatography using 5% of methanol in methylene chloride. The pure fraction was concentrated and then dissolved in methylene chloride (2 mL). A solution of hydrogen chloride in ether (1 mL, 1N) was added. Solvents were evaporated and the residue was triturated with ether and petroleum ether. The solid material was filtered to give the desired compound as hydrochloride salt (41 mg). LC-MS showed a single peak, $C_{25}H_{30}BrN_3$ (m/e) calculated 451.1623, observed 452.0 (M+H). $^1$H-NMR (CD$_3$OD) □ 8.31 (d, 1H), 7.53 (s, 1H), 7.44 (d, 1H), 7.40 (s, 1H), 7.30 (d, 1H), 7.15 (d, 1H), 4.68 (m, 1H), 3.62 (br s, 1H), 3.19-3.35 (m, 4H), 3.08 (m, 1H), 2.94 (s, 3H), 2.85 (m, 2H), 2.58 (m, 2H), 2.52 (s, 3H), 2.42 (br d, 2H), 2.07-2.24 (m, 4H).

Example 5 cis-(S)-(5-Bromo-indan-2-ylmethyl)-[3-(2,5-dimethyl-benzoimidazol-1-yl)-cyclopentyl]-amine

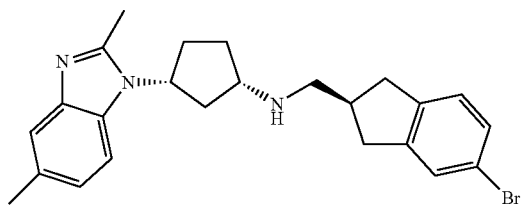

This compound was prepared from cis-3-(2,5-dimethyl-benzoimidazol-1-yl)-cyclopentylamine hydrochloride and (S)-5-bromo-indan-2-carbaldehyde using the same reductive amination method described in previous example. $^1$H-NMR is consistent with the assigned structure. LC-MS showed a single peak, $C_{24}H_{28}BrN_3$ (m/e) calcd 437.1467, obsd 438.1 (M+H).

Example 6 cis-(5-Chloro-indan-2-yl)-[4-(2,5-dimethyl-benzoimidazol-1-yl)-cyclohexyl]-amine; hydrochloride

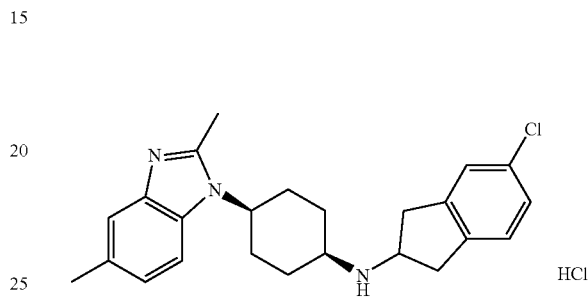

This compound was prepared with the same method as the preparation of cis-4-(2,5-dimethyl-benzoimidazol-1-yl)-cyclohexyl-indan-2-yl-amine described in previous example. $^1$H-NMR is consistent with the assigned structure, LRMS for $C_{24}H_{28}ClN_3$ (m/e) calcd 393.1972, obsd 394.3 (M+H)

Example 7 cis-(S)-2-(1-{4-[(5-Bromo-indan-2-ylmethyl)-amino]-cyclohexyl}-5-chloro-1H-benzoimidazol-2-yl)-propan-2-ol

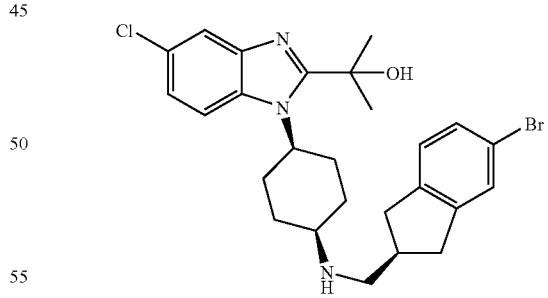

This compound was prepared from the hydrochloride salt of cis-2-[1-(4-amino-cyclohexyl)-5-chloro-1H-benzoimidazol-2-yl]-propan-2-ol and (S)-5-bromo-indan-2-carbaldehyde. LC-MS showed a single peak, $C_{26}H_{31}BrClN_3O$ (m/e) calcd 515.1339, obsd 516.1 (M+H). $^1$H-NMR (CD$_3$OD) □ 7.96 (d, 1H), 7.59 (s, 1H), 7.36 (s, 1H), 7.26 (d, 1H), 7.18 (d, 1H), 7.12 (d, 1H), 5.38 (m, 1H), 3.16 (m, 2H), 3.03 (br s, 1H), 2.67-2.83 (m, 7H), 2.07 (m, 2H), 1.72 (br s, 10H).

Example 8 cis-2-(5-Chloro-1-{4-[(5-trifluoromethyl-indan-2-ylmethyl)-amino]-cyclohexyl}-1H-benzoimidazol-2-yl)-propan-2-ol

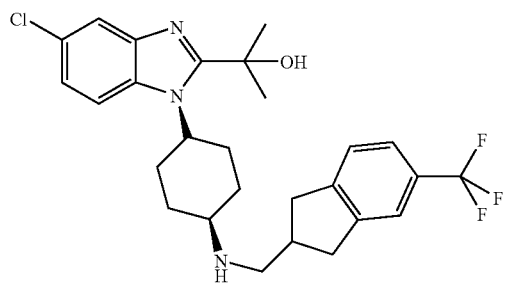

This compound was prepared from the hydrochloride salt of cis-2-[1-(4-amino-cyclohexyl)-5-chloro-1H-benzoimidazol-2-yl]-propan-2-ol and 5-trifluoromethyl-indan-2-carbaldehyde. $^1$H-NMR is consistent with the assigned structure, LC-MS showed a single peak, $C_{27}H_{31}ClF_3N_3O$ (m/e) calcd 505.2108, obsd 506.1 (M+H).

Example 9 cis-2-(5-Chloro-1-{4-[(indan-2-ylmethyl)-amino]-cyclohexyl}-1H-benzoimidazol-2-yl)-propan-2-ol

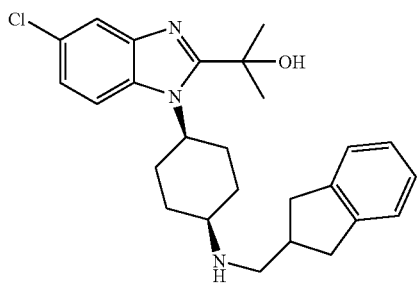

This compound was prepared from the hydrochloride salt of cis-2-[1-(4-amino-cyclohexyl)-5-chloro-1H-benzoimidazol-2-yl]-propan-2-ol and indan-2-carbaldehyde. $^1$H-NMR is consistent with the assigned structure, LC-MS showed a single peak, $C_{26}H_{32}ClN_3O$ (m/e) calcd 437.2234, obsd 438.2 (M+H).

Example 10 cis-2-(5-Chloro-1-{4-[(5-chloro-indan-2-ylmethyl)-amino]-cyclohexyl}-1H-benzoimidazol-2-yl)-propan-2-ol

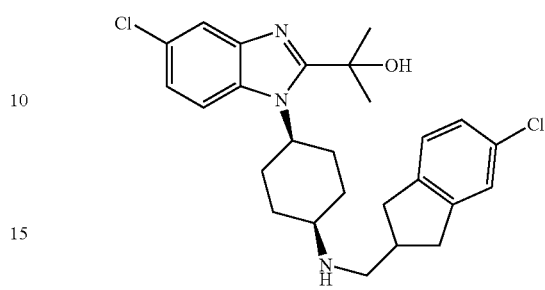

This compound was prepared from the hydrochloride salt of cis-2-[1-(4-amino-cyclohexyl)-5-chloro-1H-benzoimidazol-2-yl]-propan-2-ol and 5-chloro-indan-2-carbaldehyde. $^1$H-NMR is consistent with the assigned structure, LC-MS showed a single peak, $C_{26}H_{31}Cl_2N_3O$ (m/e) calcd 471.1844, obsd 472.1 (M+H).

Example 11 cis-(5-Chloro-indan-2-ylmethyl)-[4-(2,5-dimethyl-benzoimidazol-1-yl)-cyclohexyl]-amine

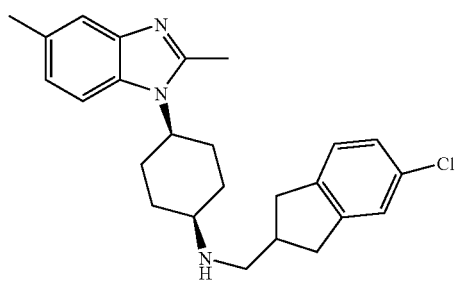

This compound was prepared from the hydrochloride salt of cis-4-(2,5-dimethyl-benzoimidazol-1-yl)-cyclohexylamine and 5-chloro-indan-2-carbaldehyde. $^1$H-NMR is consistent with the assigned structure, LC-MS showed a single peak, $C_{25}H_{30}ClN_3$ (m/e) calcd 407.2128, obsd 408.2 (M+H).

Example 12 cis-[4-(2,5-Dimethyl-benzoimidazol-1-yl)-cyclohexyl]-(5-trifluoromethyl-indan-2-ylmethyl)-amine

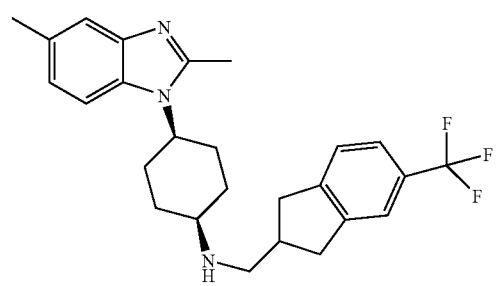

This compound was prepared from the hydrochloride salt of cis-4-(2,5-dimethyl-benzoimidazol-1-yl)-cyclohexylamine and 5-trifluoromethyl-indan-2-carbaldehyde. $^1$H-NMR is consistent with the assigned structure, LC-MS showed a single peak, $C_{26}H_{30}F_3N_3$ (m/e) calcd 441.2392, obsd 442.2 (M+H).

Example 13 cis-[4-(2,5-Dimethyl-benzoimidazol-1-yl)-cyclohexyl]-indan-2-ylmethyl-amine

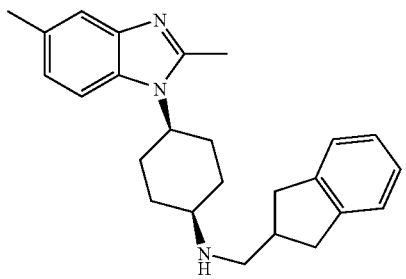

This compound was prepared from the hydrochloride salt of cis-4-(2,5-dimethyl-benzoimidazol-1-yl)-cyclohexylamine and indan-2-carbaldehyde. $^1$H-NMR is consistent with the assigned structure, LC-MS showed a single peak, $C_{25}H_{31}N_3$ (m/e) calcd 373.2518, obsd 374.2 (M+H).

Example 14 cis-(S)-2-({4-[5-Chloro-2-(1-hydroxy-1-methyl-ethyl)-benzoimidazol-1-yl]-cyclohexylamino}-methyl)-indan-5-carbonitrile

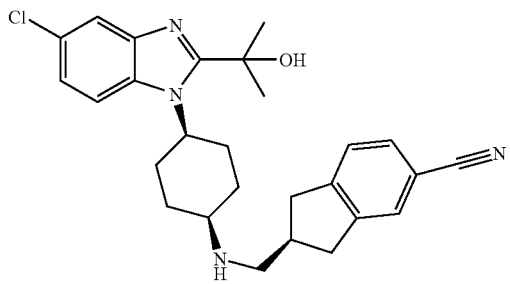

This compound was prepared from the hydrochloride salt of cis-2-[1-(4-amino-cyclohexyl)-5-chloro-1H-benzoimidazol-2-yl]-propan-2-ol and (S)-5-cyano-indan-2-carbaldehyde. LC-MS showed a single peak, $C_{27}H_{31}ClN_4O$ (m/e) calcd 462.2186, obsd 463.2 (M+H). $^1$H-NMR (CD$_3$OD) □ 7.96 (d, 1H), 7.59 (s, 1H), 7.57 (s, 1H), 7.49 (d, 1H), 7.38 (d, 1H), 7.18 (d, 1H), 5.38 (m, 1H), 3.22 (m, 2H), 2.75-2.97 (m, 8H), 2.01 (m, 2H), 1.72 (s, 6H), 1.68 (m, 4H).

Example 15 cis-(S)-2-{[4-(2,5-Dimethyl-benzoimidazol-1-yl)-cyclohexylamino]-methyl}-indan-5-carbonitrile

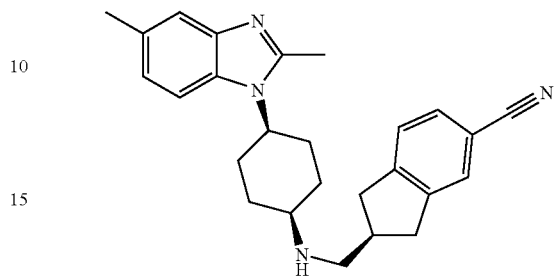

This compound was prepared from the hydrochloride salt of cis-4-(2,5-dimethyl-benzoimidazol-1-yl)-cyclohexylamine and (S)-5-cyano-indan-2-carbaldehyde. $^1$H-NMR is consistent with the assigned structure, LC-MS showed a single peak, $C_{26}H_{30}N_4$ (m/e) calcd 398.2470, obsd 399.3 (M+H).

Example 16 cis-(S)-2-({4-[2-(1-Hydroxy-1-methyl-ethyl)-5-methyl-benzoimidazol-1-yl]-cyclohexylamino}-methyl)-indan-5-carbonitrile

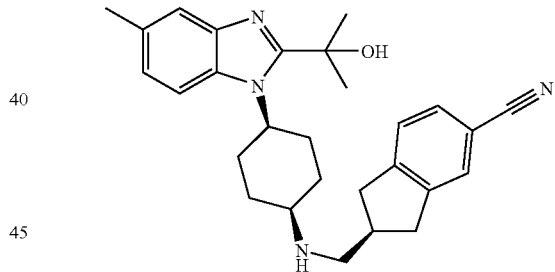

This compound was prepared from the hydrochloride salt of 2-[1-(4-amino-cyclohexyl)-5-methyl-1H-benzoimidazol-2-yl]-propan-2-ol (prepared as cis/trans-isomer mixture) and (S)-2-formyl-indan-5-carbonitrile through the same reductive amination method described previously. The crude mixture was separated through flash column chromatography using methylene chloride and methanol (20:1 to 10:1). The fraction with less retention time (higher $R_f$) gave cis-(S)-2-({4-[2-(1-hydroxy-1-methyl-ethyl)-5-methyl-benzoimidazole-1-yl]-cyclohexylamino}-methyl)-indan-5-carbonitrile. The analysis of the $^1$H-NMR confirmed the cis-conformation of the cyclohexane. LC-MS showed a single peak, $C_{28}H_{34}N_4O$ (m/e) calcd 442.2733, obsd 443.3 (M+H). $^1$H-NMR (CD$_3$OD) □ 7.82 (d, 1H), 7.55 (s, 1H), 7.49 (d, 1H), 7.41 (s, 1H), 7.38 (d, 1H), 7.03 (d, 1H), 5.30 (m, 1H), 3.23 (m, 2H), 2.71-2.93 (m, 8H), 2.43 (s, 3H), 1.98 (br d, 2H), 1.72 (s, 6H), 1.64 (m, 4H).

Example 17 trans-(S)-2-({4-[2-(1-Hydroxy-1-methyl-ethyl)-5-methyl-benzoimidazol-1-yl]-cyclohexylamino}-methyl)-indan-5-carbonitrile

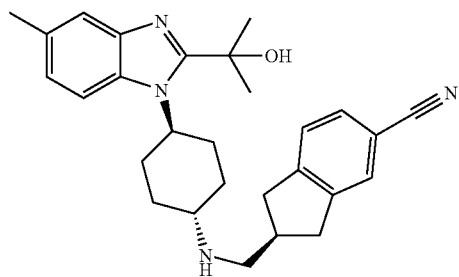

This compound was isolated as the second isomer (later fraction) in the preparation of cis-(S)-2-({4-[2-(1-hydroxy-1-methyl-ethyl)-5-methyl-benzoimidazole-1-yl]-cyclohexylamino}-methyl)-indan-5-carbonitrile. The analysis of the $^1$H-NMR confirmed the trans-conformation of the cyclohexane. LC-MS showed a single peak, $C_{28}H_{34}N_4O$ (m/e) calcd 442.2733, obsd 443.2 (M+H).

Example 18 cis-2-(1-{4-[(5-Fluoro-indan-2-ylmethyl)-amino]-cyclohexyl}-5-methyl-1H-benzoimidazol-2-yl)-propan-2-ol

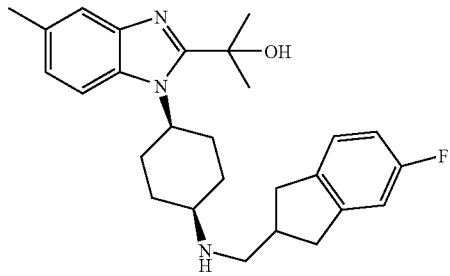

This compound was prepared from the hydrochloride salt of 2-[1-(4-amino-cyclohexyl)-5-methyl-1H-benzoimidazol-2-yl]-propan-2-ol (prepared as cis/trans-isomer mixture) and 5-fluoro-indan-2-carbaldehyde. The less polar of the two substances isolated by chromatography gave cis-2-(1-{4-[(5-fluoro-indan-2-ylmethyl)-amino]-cyclohexyl}-5-methyl-1H-benzoimidazol-2-yl)-propan-2-ol. The analysis of the $^1$H-NMR confirmed the cis-conformation of the cyclohexane. LC-MS showed a single peak, $C_{27}H_{34}FN_3O$ (m/e) calcd 435.2686, obsd 436.3 (M+H).

Example 19 trans-2-(1-{4-[(5-Fluoro-indan-2-ylmethyl)-amino]-cyclohexyl}-5-methyl-1H-benzoimidazol-2-yl)-propan-2-ol

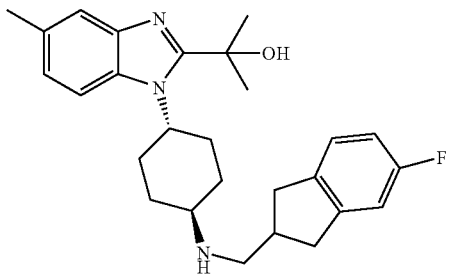

This compound was isolated as the second and more polar product in the preparation of cis-2-(1-{4-[(5-fluoro-indan-2-ylmethyl)-amino]-cyclohexyl}-5-methyl-1H-benzoimidazol-2-yl)-propan-2-ol. The analysis of the $^1$H-NMR confirmed the trans-conformation of the cyclohexane. LC-MS showed a single peak, $C_{27}H_{34}FN_3O$ (m/e) calcd 435.2686, obsd 436.3 (M+H).

Example 20 cis-2-(1-{4-[(5-Chloro-indan-2-ylmethyl)-amino]-cyclohexyl}-5-methyl-1H-benzoimidazol-2-yl)-propan-2-ol

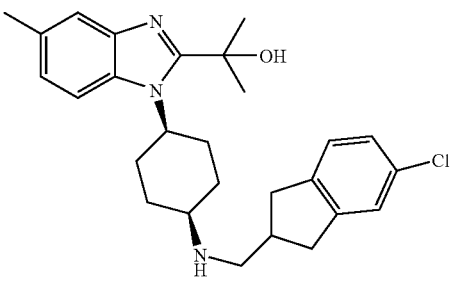

This compound was prepared from the hydrochloride salt of 2-[1-(4-amino-cyclohexyl)-5-methyl-1H-benzoimidazol-2-yl]-propan-2-ol (prepared as cis/trans-isomer mixture) and 5-chloro-indan-2-carbaldehyde. The less polar of the two substances isolated by chromatography gave cis-2-(1-{4-[(5-chloro-indan-2-ylmethyl)-amino]-cyclohexyl}-5-methyl-1H-benzoimidazol-2-yl)-propan-2-ol. The analysis of the $^1$H-NMR confirmed the cis-conformation of the cyclohexane. LC-MS showed a single peak, $C_{27}H_{34}ClN_3O$ (m/e) calcd 451.2390, obsd 452.3 (M+H). $^1$H-NMR (CD$_3$OD) ☐ 7.83 (d, 1H), 7.40 (s, 1H), 7.20 (s, 1H), 7.17 (d, 1H), 7.10 (d, 1H), 7.03 (d, 1H), 5.32 (m, 1H), 3.16 (m, 2H), 2.96 (br s, 1H), 2.73-2.85 (m, 7H), 2.43 (s, 3H), 2.00 (m, 2H), 1.72 (s, 6H), 1.68 (m, 4H).

Example 21 trans-2-(1-{4-[(5-Chloro-indan-2-ylmethyl)-amino]-cyclohexyl}-5-methyl-1H-benzoimidazol-2-yl)-propan-2-ol

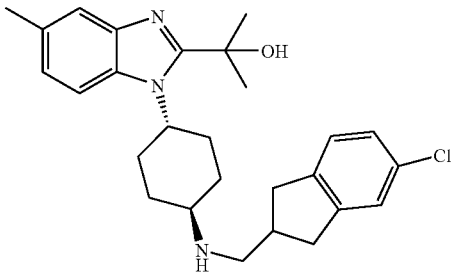

This compound was isolated as the second and more polar substance in the preparation of cis-2-(1-{4-[(5-chloro-indan-2-ylmethyl)-amino]-cyclohexyl}-5-methyl-1H-benzoimidazol-2-yl)-propan-2-ol. The analysis of the $^1$H-NMR confirmed the trans-conformation of the cyclohexane. LC-MS showed a single peak, $C_{27}H_{34}ClN_3O$ (m/e) calcd 451.2390, obsd 452.3 (M+H).

Example 22 cis-(R)-2-({4-[5-Chloro-2-(1-hydroxy-1-methyl-ethyl)-benzoimidazol-1H-yl]-cyclohexylamino}-methyl)-indan-5-carbonitrile

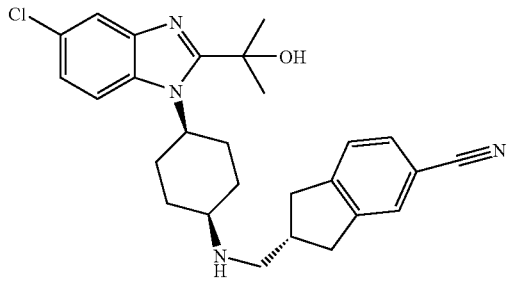

This compound was prepared from the hydrochloride salt of cis-2-[1-(4-amino-cyclohexyl)-5-chloro-1H-benzoimidazol-2-yl]-propan-2-ol and (R)-5-cyano-indan-2-carbaldehyde. $^1$H-NMR is consistent with the assigned structure, LC-MS showed a single peak, $C_{27}H_{31}ClN_4O$ (m/e) calcd 462.2186, obsd 463.2 (M+H).

Example 23 cis-(S)—N-{4-[5-Chloro-2-(1-hydroxy-1-methyl-ethyl)-benzoimidazol-1-yl]-cyclohexyl}-N-(5-cyano-indan-2-ylmethyl)-acetamide

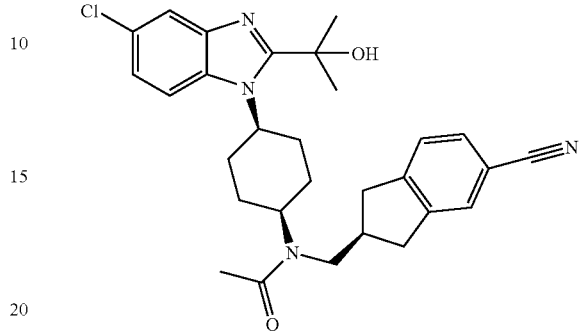

To a solution of cis-(S)-2-({4-[5-chloro-2-(1-hydroxy-1-methyl-ethyl)-benzoimidazol-1-yl]-cyclohexylamino}-methyl)-indan-5-carbonitrile (25 mg, 0.054 mmol) in methylene chloride (5 mL) was added triethylamine (11 mg, 0.108 mmol), acetyl chloride (5 mg, 0.063 mmol) and trace amount of 4-dimethylaminopyridine. The mixture was stirred at room temperature for 65 hours. The reaction mixture was diluted with dichloromethane and the solution was washed with saturated aqueous sodium bicarbonate solution followed by brine. The organic extract was dried over sodium sulfate, filtered and evaporated under reduced pressure. The residue was subjected to column chromatography, eluting with dichloromethane and ethyl acetate in the presence of 4% methanol to give cis-(S)—N-{4-[5-chloro-2-(1-hydroxy-1-methyl-ethyl)-benzoimidazol-1-yl]-cyclohexyl}-N-(5-cyano-indan-2-ylmethyl)-acetamide (15 mg). LC-MS showed a single peak, $C_{29}H_{33}ClN_4O_2$ (m/e) calcd 504.2292, obsd 505.3. $^1$H-NMR (CD$_3$OD) □ 7.67 (br, 1H) 7.59 (s, 2H), 7.50 (d, 1H), 7.40 (d, 1H), 7.23 (d, 1H), 5.57 (m, 1H), 3.48 (br d, 2H), 3.15 (m, 2H), 2.97 (m, 1H), 2.84 (m, 2H), 2.59 (br, 2H), 2.32 (br, 1H), 2.11 (br s, 2H), 1.93 (m, 4H), 1.72 (s, 6H), 1.28 (s, 3H).

Example 24 cis-(R)-2-(1-{4-[(5-Bromo-indan-2-ylmethyl)-amino]-cyclohexyl}-5-chloro-1H-benzoimidazol-2-yl)-propan-2-ol

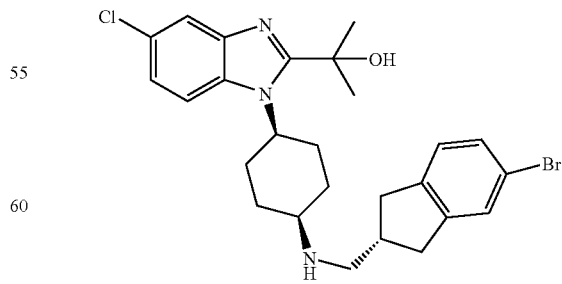

This compound was prepared from the hydrochloride salt of cis-2-[1-(4-amino-cyclohexyl)-5-chloro-1H-benzoimidazol-2-yl]-propan-2-ol and (R)-5-bromo-indan-2-carbaldehyde. ¹H-NMR is consistent with the assigned structure, LC-MS showed a single peak, $C_{26}H_{31}BrClN_3O$ (m/e) calcd 515.1339, obsd 516.2 (M+H).

Example 25 cis-1-{4-[(5-Chloro-indan-2-ylmethyl)-amino]-cyclohexyl}-2-methyl-1H-benzoimidazole-5-carbonitrile

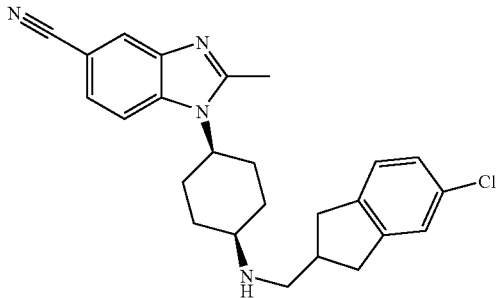

This compound was prepared from the hydrochloride salt of cis-1-(4-amino-cyclohexyl)-2-methyl-1H-benzoimidazole-5-carbonitrile and 5-chloro-indan-2-carbaldehyde. ¹H-NMR is consistent with the assigned structure, LC-MS showed a single peak, $C_{25}H_{27}ClN_4$ (m/e) calcd 418.1924, obsd 419.2 (M+H).

Example 26 cis-(S)-2-{[4-(5-Fluoro-2-methyl-benzoimidazol-1-yl)-cyclohexylamino]-methyl}-indan-5-carbonitrile

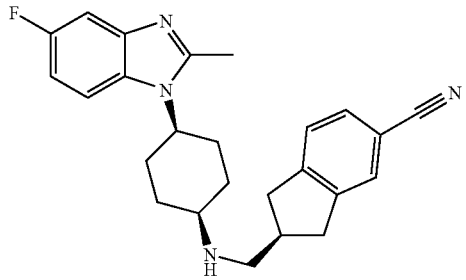

This compound was prepared from the hydrochloride salt of cis-4-(5-fluoro-2-methyl-benzoimidazol-1-yl)-cyclohexylamine and (S)-2-formyl-indan-5-carbonitrile through the same reductive amination method described previously. LC-MS showed a single peak, $C_{25}H_{27}FN_4$ (m/e) calcd 402.2220, obsd 403.2 (M+H). ¹H-NMR (CD₃OD) δ 7.82 (q, 1H), 7.56 (s, 1H), 7.48 (d, 1H), 7.39 (d, 1H), 7.22 (d, 1H), 6.99 (t, 1H), 4.37 (m, 1H), 3.25 (m, 2H), 2.96 (br s, 1H), 2.65-2.90 (m, 7H), 2.61 (s, 3H), 1.99 (br d, 2H), 1.74 (m, 2H), 1.65 (br d, 2H).

Example 27

MCHR Filter Binding Assay

Competition binding assay was conducted in MultiScreen 0.65 μM glass fiber type B filter plates (96-well, Millipore). The MultiScreen plates were pretreated by incubation with 0.5% polyvinylpyrrolidone solution containing 1% BSA and 0.1% tween-20 for 12 hours at 4° C. and washed five times with ice-cold 10 mM Tris buffer, pH 7.5, followed by incubation with 200 μL of binding buffer (50 mM HEPES, 2.5 mM $CaCl_2$, 0.05 mM BSA, 1 mM phenanthroline, 0.03 mM Triton X-100) for 5 min at room temperature and plates were drained before the binding reactions. The binding assay was performed by pre-incubating 2.8 μg of membranes from CHO-K1 cells stably expressing the recombinant human MCHR1 receptors, and various concentrations (final concentration 0.059 nM to 45 μM) of unlabeled MCH or antagonists in binding buffer for 15 min at room temperature. The competition reaction was started by adding final concentration (0.2 nM) [Phe¹³[¹²⁵I]Tyr¹⁹]-MCH (PerkinElmer). The final volume of the reaction was 90 μL per well. After 60 min incubation time at room temperature the reaction was stopped by rapid filtration over 96-well filter plates. Following termination of the binding reactions, the filters were washed with ice-cold binding buffer (4×200 μL), and were air dried for 30 min. Scintillation cocktail (60 μL) was added to each well and radioactivity bound to the plates was determined using a Micro-beta plate reader (Wallace/PerkinElmer). The inhibition potency of antagonist was expressed as $IC_{50}$, the concentration of compound at which the binding of radio labeled MCH to MCHR1 was inhibited by 50%. The potency is listed in the following table:

| Example | Activity in MCHR binding assays<br>A = $IC_{50}$ < 0.01 μM; B = $IC_{50}$ < 0.1 μM; C = $IC_{50}$ < 1 μM |
|---|---|
| 1 | C |
| 2 | C |
| 3 | C |
| 4 | B |
| 5 | C |
| 6 | B |
| 7 | B |
| 8 | C |
| 9 | B |
| 10 | B |
| 11 | B |
| 12 | C |
| 13 | C |
| 14 | A |
| 15 | B |
| 16 | A |
| 17 | C |
| 18 | B |
| 19 | C |
| 20 | B |
| 21 | C |
| 22 | A |
| 23 | C |
| 24 | B |
| 25 | B |
| 26 | A |

Five compounds were selected from the examples in Part II above. These five compounds were assayed for their inhibition activity against the binding of MCH to MCHR, the results of which are shown in the table below:

| Example | MCHR $IC_{50}$ (nM) | Ki (nM) |
|---|---|---|
| 7 | 24 | 19 |
| 14 | 2.2 | 1.8 |
| 20 | 26 | 21 |
| 23 | 193 | 154 |
| 26 | 3.0 | 2.0 |

What is claimed is:

1. A compound of formula (I):

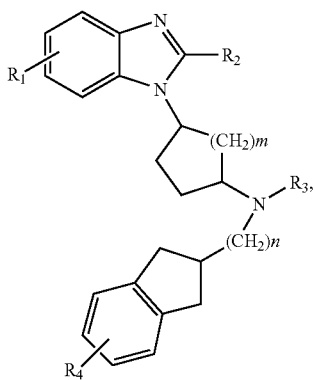

wherein:
R₁ is hydrogen, lower alkyl, halo or cyano;
R₂ is hydrogen, lower alkyl, alkoxy or hydroxyalkyl;
R₃ is hydrogen, lower alkyl, lower alkyl carbonyl or aryl;
R₄ is hydrogen, lower alkyl, halo, lower alkylhalo or cyano;
m is 1 or 2; and
n is 0 or 1,
and pharmaceutically acceptable salts thereof.

2. The compound according to claim 1, wherein
R₁ is lower alkyl, halo or cyano; and
R₃ is hydrogen or lower alkyl.

3. The compound according to claim 1, wherein
R₂ is lower alkyl, alkoxy or hydroxyalkyl; and
R₄ is halo or cyano.

4. The compound according to claim 1, wherein R₁ is methyl or chloro.

5. The compound according to claim 1, wherein R₂ is methyl, propan-2-ol or trifluoromethyl.

6. The compound according to claim 1, wherein R₃ is hydrogen or acetyl.

7. The compound according to claim 1, wherein R₄ is hydrogen, bromo, chloro, fluoro, trifluoromethyl or cyano.

8. The compound according to claim 1, wherein said compound is cis-(S)-2-(1-{4-[(5-Bromo-indan-2-ylmethyl)-amino]-cyclohexyl}-5-chloro-1H-benzoimidazol-2-yl)-propan-2-ol.

9. The compound according to claim 1, wherein said compound is cis-2-(5-Chloro-1-{4-[(indan-2-ylmethyl)-amino]-cyclohexyl}-1H-benzoimidazol-2-yl)-propan-2-ol.

10. The compound according to claim 1, wherein said compound is cis-(5-Chloro-indan-2-ylmethyl)-[4-(2,5-dimethyl-benzoimidazol-1-yl)-cyclohexyl]-amine.

11. The compound according to claim 1, wherein said compound is cis-(S)-2-({4-[5-Chloro-2-(1-hydroxy-1-methyl-ethyl)-benzoimidazol-1-yl]-cyclohexylamino}-methyl)-indan-5-carbonitrile.

12. The compound according to claim 1, wherein said compound is cis-(S)-2-{[4-(2,5-Dimethyl-benzoimidazol-1-yl)-cyclohexylamino]-methyl}-indan-5-carbonitrile.

13. The compound according to claim 1, wherein said compound is cis-(S)-2-({4-[2-(1-Hydroxy-1-methyl-ethyl)-5-methyl-benzoimidazol-1-yl]-cyclohexylamino}-methyl)-indan-5-carbonitrile.

14. The compound according to claim 1, wherein said compound is cis-2-(1-{4-[(5-Chloro-indan-2-ylmethyl)-amino]-cyclohexyl}-5-methyl-1H-benzoimidazol-2-yl)-propan-2-ol.

15. The compound according to claim 1, wherein said compound is cis-(S)—N-{4-[5-Chloro-2-(1-hydroxy-1-methyl-ethyl)-benzoimidazol-1-yl]-cyclohexyl}-N-(5-cyano-indan-2-ylmethyl)-acetamide.

16. The compound according to claim 1, wherein said compound is cis-(R)-2-({4-[5-Chloro-2-(1-hydroxy-1-methyl-ethyl)-benzoimidazol-1H-yl]-cyclohexylamino}-methyl)-indan-5-carbonitrile.

17. The compound according to claim 1, wherein said compound is cis-(S)-2-{[4-(5-Fluoro-2-methyl-benzoimidazol-1-yl)-cyclohexylamino]-methyl}-indan-5-carbonitrile.

18. A pharmaceutical composition comprising a therapeutically effective amount of a compound according to claim 1 or a pharmaceutically acceptable salt thereof, and a pharmaceutically acceptable carrier.

19. A method for treating obesity, comprising administering a therapeutically effective amount of a compound or a pharmaceutically acceptable salt thereof according to claim 1 to a patient in need thereof.

* * * * *